(12) United States Patent
Kuo

(10) Patent No.: US 10,561,696 B2
(45) Date of Patent: Feb. 18, 2020

(54) MULTI-CAROTENOIDS COMPOSITIONS AND USES THEREFOR

(71) Applicant: HEALTH-EVER BIOTECH CO. LTD, Taipei (TW)

(72) Inventor: Fu Feng Kuo, Richmond (CA)

(73) Assignee: HEALTH-EVER BIOTECH CO. LTD, Taipei (TW)

( * ) Notice: Subject to any disclaimer, the term of this patent is extended or adjusted under 35 U.S.C. 154(b) by 1187 days.

(21) Appl. No.: 14/658,060

(22) Filed: Mar. 13, 2015

(65) Prior Publication Data

US 2015/0182576 A1 Jul. 2, 2015

Related U.S. Application Data

(63) Continuation of application No. 12/479,094, filed on Jun. 5, 2009, now Pat. No. 9,044,407, which is a continuation-in-part of application No. 11/695,354, filed on Apr. 2, 2007, now abandoned.

(30) Foreign Application Priority Data

Apr. 3, 2006 (TW) ............................... 95111722 A

(51) Int. Cl.
| | | |
|---|---|---|
| A61K 36/81 | (2006.01) | |
| A23L 33/105 | (2016.01) | |
| A61K 9/48 | (2006.01) | |
| A61K 36/42 | (2006.01) | |
| A61K 36/48 | (2006.01) | |
| A61K 36/87 | (2006.01) | |
| A61K 31/01 | (2006.01) | |
| A61K 31/66 | (2006.01) | |
| A23L 5/44 | (2016.01) | |
| A23L 33/11 | (2016.01) | |
| A61K 31/015 | (2006.01) | |
| A61K 31/56 | (2006.01) | |
| A61K 31/685 | (2006.01) | |
| A61K 31/355 | (2006.01) | |
| A61K 31/575 | (2006.01) | |
| A61K 31/661 | (2006.01) | |

(52) U.S. Cl.
CPC ............... *A61K 36/81* (2013.01); *A23L 5/44* (2016.08); *A23L 33/105* (2016.08); *A23L 33/11* (2016.08); *A61K 9/4858* (2013.01); *A61K 9/4875* (2013.01); *A61K 31/01* (2013.01); *A61K 31/015* (2013.01); *A61K 31/355* (2013.01); *A61K 31/56* (2013.01); *A61K 31/575* (2013.01); *A61K 31/66* (2013.01); *A61K 31/661* (2013.01); *A61K 31/685* (2013.01); *A61K 36/42* (2013.01); *A61K 36/48* (2013.01); *A61K 36/87* (2013.01)

(58) Field of Classification Search
None
See application file for complete search history.

(56) References Cited

U.S. PATENT DOCUMENTS

| | | |
|---|---|---|
| 2003/0104078 A1 | 6/2003 | Barrett-Reis et al. |
| 2005/0031557 A1* | 2/2005 | Gaertner ............... A61K 31/07 424/59 |

OTHER PUBLICATIONS

Kucuk et al., Effects of Lycopene Supplementation in Patients with Localized Prostate Cancer, 2002, Exp Biol Med, 227:881-885.*
Pavelic et al., Prostata-Promjene Pre;azne Zone. Etiologija, Regulacija Rasta, Cimbenici Rasta, Geneticke Promjene, 2002, Lijec Vjesn; godiste 124, 211-219.*
Final Office Action issued in U.S. Appl. No. 12/545,287 dated Mar. 24, 2017 (11 pages).
Non-Final Office Action issued in related U.S. Appl. No. 12/545,287 dated Aug. 31, 2016 (59 pages).

* cited by examiner

Primary Examiner — Terry A McKelvey
Assistant Examiner — Catheryne Chen
(74) Attorney, Agent, or Firm — Maier & Maier, PLLC

(57) ABSTRACT

Methods for ameliorating the effects of benign prostate hyperplasia (BPH)-related lower urinary tract symptoms (LUTS) in men, comprising orally administering an effective amount of multi-carotenoids compositions. Multi-carotenoids composition for oral administration comprising about 71% by weight, of a tomato extract containing therein about 2% to 10% by weight of lycopene, about 0.25% to 2% by weight of phytoene, and about 0.2% to 2% by weight of phytofluene, and about 29% by weight, of a suitable encapsulating matrix. A suitable encapsulating matrix is an edible oil exemplified by soya oil, pumpkin seed oil, grape-seed oil and the like. The tomato extract may additionally comprise one or more of at least one carotene selected from the group comprising β-carotene, γ-carotene, and δ-carotene, a phytosterol, a tocopheral and a phospholipid. Use of multi-carotenoids compositions for the treatment of urinary tract malfunctions including benign prostate hyperplasia and lower urinary tract symptoms.

20 Claims, 3 Drawing Sheets

MULTI-CAROTENOIDS COMPOSITIONS AND USES THEREFOR

This application is a continuation of U.S. application Ser. No. 12/479,094, filed on Jun. 5, 2009, which is a continuation-in-part application of U.S. application Ser. No. 11/695,354, filed on Apr. 2, 2007, which claims the benefit of priority from Taiwanese Patent Application No. 095111722, filed on Apr. 3, 2006, the disclosure of all of which re incorporated by reference herein in their entirety.

TECHNICAL FIELD

This invention relates to compositions comprising a plurality of carotenoid compounds and methods for oral administration of carotenoids compositions for ameliorating the effects of aging-related urinary impairments and malfunctions in men. More particularly, the present invention is directed to compostions comprising at least lycopene, phytoene and phytofluene, for oral administration as a nutritional supplement and/or a botanical drug. The present invention also relates to methods for use of said compositions disclosed herein.

BACKGROUND OF THE INVENTION

Lycopene and its precursor phytofluene are carotenoids commonly found in tomatoes and are the predominant sources of the bright red color associated with tomatoes. Phytoene is a precursor to phytofluene, lycopene and other carotenoids, and is also found in high concentrations in tomatoes. Lycopene is generally present in the plasma of the human body; the serum concentrations of lycopene are typically about 2.5 times higher than those of $\alpha$-carotene and 7.5 times greater than those of $\beta$-carotene. Carotenoids are known to have antioxidant properties and consequently, provide numerous beneficial health effects including reducing the potential risks of cardiovascular diseases, cancers, and slowing and/or reversing the degenerative effects of aging on various human physiological activities.

Carotenoids are a group of pigments that are characterized by the color including and ranging from yellow to red. Carotenoids am commonly produced by a wide variety of plant materials and most commonly associated with plants such as tomatoes, carrots and peppers.

Benign prostates hyperplasia (also called BPH) and prostate cancer are aging-related conditions that affect prostate gland physiology and impair urinary function in men. As many men age, their prostate glands slowly enlarge causing (a) obstructive symptoms exemplified by weak and/or intermittent urinary streams, a sense of residual urine in the bladder after voiding, and dribbling or leakage at the end of urination, and/or (b) irritative symptoms as exemplified by urgency of micturation, increased frequency of urination, and uracratia. Obstructive and irritative urinary symptom are commonly referred to as lower urinary tract symptoms (LUTS). The current treatments of prostate cancer, BPH and LUTS symptoms consist of drug therapies and major surgery. The two primary drug classes used are alpha-blockers and 5-alpha-reductase inhibitors, which should be taken for life in order to get the persistent efficacy. When surgery is considered, the results are usually positive, but there are risks associated with such surgical operations.

SUMMARY OF THE INVENTION

Embodiments of the present invention relate to multi-carotenoids compositions for oral administration as nutritional supplements or botanical drugs, wherein the compositions comprise at least lycopene, phytoene, phytofluene components, and a suitable carrier.

According to one embodiment, there are provided methods for oral administration of multi-carotenoids compositions for ameliorating the effects of aging-related urinary impairments and malfunctions in men. Such urinary impairments and malfunctions are exemplified by benign prostatic hyperplasia and lower urinary tract symptoms such as obstructive symptoms and irritative symptoms, and the like. The multi-carotenoids compositions for oral administration comprise at least lycopene, phytoene, phytofluene components, and a suitable carrier.

Another embodiment relates to methods for ameliorating the effects of aging-related urinary tract malfunctions in men, where the urinary tract malfunctions comprise the group of benign prostate hyperplasia and lower urinary tract symptoms, and the method comprises orally administrating an effective amount of a composition comprising:

a tomato extract comprising about 2% to 10% by weight of lycopene, about 0.25% to 2% by weight of phytoene, and about 0.2% to 2% by weight of phytofluene;

an edible oil; and a suitable carrier.

In one embodiment, the multi-carotenoids compositions are nutritional supplements and/or botanical drugs.

According to one aspect, the lycopene, phytoene, and phytofluene components of the multi-carotenoid compositions are preferably naturally occurring and are preferably extracted from tomatoes as pulp. The tomato pulp is further processed into oleoresins, beadlets, dry powder materials, paste and combinations thereof.

In one embodiment, the tomato extract and edible oil are further processed into soft-gel capsules, or alternatively, in "hard" capsules, or optionally, configured into tablets, or if so desired, into sachet packets, beverages, and combinations thereof.

According to another aspect, the tomato extracts comprising the multi-carotenoids compositions of the present invention may additionally contain one or more of $\beta$-carotene, $\gamma$-carotene, and $\delta$-carotene, a phytosterol, a tocopheral and a phospholipid.

In one embodiment, the multi-carotenoids compositions comprise lycopene, phytoene, phytofluene, and vitamin E components with trace amounts of $\beta$-carotene, $\gamma$-carotene, and $\delta$-carotene, within a tomato oil matrix. This matrix is encased in a soft gel capsule. The composition may additionally comprise an edible oil exemplified by soya oil, pumpkin seed oil, grapeseed oil and the like. Alternatively, the matrix is encased in a hard capsule.

A further embodiment relates to the use of multi-carotenoids compositions for the treatment of urinary tract malfunctions comprising the group of benign prostate hyperplasia and lower urinary tract symptoms. The composition comprises at least lycopene, phytoene, and phytofluene; and a suitable carrier. In another aspect, the composition comprises: a tomato extract comprising about 2% to 10% by weight of lycopene, about 0.25% to 2% by weight of phytoene, and about 0.2% to 2% by weight of phytofluene; an edible oil; and a suitable carrier. In a further aspect, the composition comprises: a tomato extract comprising about 4% to 7% by weight of lycopene, about 0.4% to 0.7% by weight of phytoene; about 03% to 0.6% by weight of phytofluene, about 1% to 3% by weight of a tocopherol, about 1% to 2% by weight of a $\beta$-carotene, about 03% to 0.6% by weight of a phytosterol, about 5% to 10% by weight of a phospholipid; an edible oil; and a suitable carrier.

BRIEF DESCRIPTION OF THE DRAWINGS

Embodiments of the present invention will be described with reference to the following drawings.

DETAILED DESCRIPTION OF THE INVENTION

Figure 1:
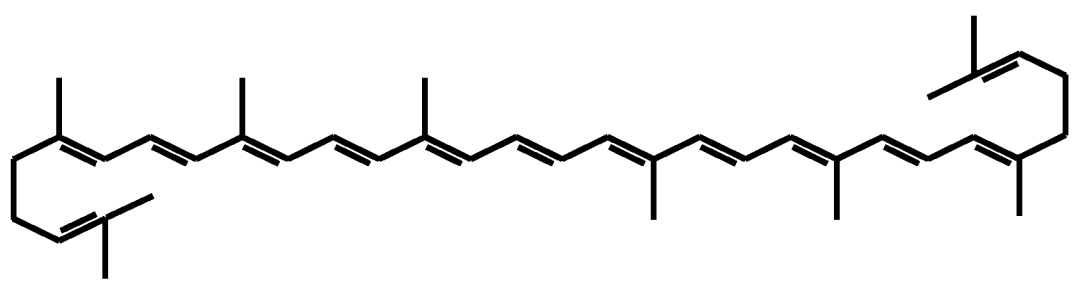
FIG. 1 is a lycopene isomer.

The present invention provides stable multi-carotenoids compositions useful for oral administration as nutritional supplements and/or botanical drugs, wherein the compositions comprise at least lycopene, phytoene, phytofluene components contained within an extract produced from tomato fruits. Suitable tomato fruits are produced by non-genetically engineered plants, and preferably contain high concentrations of lycopene. The compositions are preferably encased in a soft gel capsule and may additionally comprise an edible oil exemplified by soya oil, pumpkin seed oil, grapeseed oil and the like.

Botanical drugs are generally understood to be products intended for use in the diagnosis, cure, mitigation, treatment or prevention of disease in humans. Botanical drug products typically include vegetable materials, which may include plant materials, algae, macroscopic fungi, or combinations thereof.

The lycopene, phytoene and phytofluene components are preferably processed from tomato fruits into extracts. The components may be concentrated by removing water from the extracts thereby producing thickened pulps that contain therein the lycopene, phytoene and phytofluene components, and additionally comprise β-carotene, γ-carotene, δ-carotene, vitamin E, a plurality of phytosterols and phospholipids. The thickened pulps may be further suitably processed into oleoresin-based emulsions. The oleoresins may be encapsulated within soft gel capsules comprising soya oil or alternatively, pumpkin seed oil, grapeseed oil or combinations thereof. The tomato extracts may be optionally formulated into beadlets that may be packaged if so desired in sachet packets, or alternatively, dried and processed into powders and pastes that may be optionally encapsulated or alternatively, tabletted. Alternatively, tomato extracts may be formulated into beverages.

Lycopene in its natural state, contained within for example a tomato, does not have the same benefits as when it is extracted and formulated into a nutritional supplement or and/botanical drug.

The synergistic effect of the combination of carotenoids and other bioactive compounds such as vitamin C, vitamin E and flavonoids is known in the art to provide improved health benefits. In one embodiment, the multi-carotenoids compositions include naturally extracted carotenoids that have complex chemical structures. The multi-carotenoids compositions contain lycopene, as well as tocopherols, phytoene, phytofluene, beta-carotene and other bioactive phytochemicals. The synergistic effect of lycopene in combination with phytoene and phytofluene was compared to the effect of the administration of the same carotenoids alone. For example, on administration of a low concentration of lycopene in combination with phytoene and phytofluene, a synergistic inhibition of cancer cell growth was evident (data not shown) on comparison to the administration of lycopene alone.

In one embodiment, the multi-carotenoids composition is administered orally on a regular basis. In another embodiment, the multi-carotenoids composition is administered weekly. In an alternative embodiment, the multi-carotenoids composition is administered daily. In a further embodiment, the multi-carotenoids composition is administered every other day. In a further embodiment, the multi-carotenoids composition is administered every third day.

In one embodiment, the multi-carotenoids composition of the present invention is a soft gel capsule that is orally administered and comprises about: (a) 71% by weight of a tomato extract containing about 2% to 10% by weight of lycopene, 0.25% to 2% by weight of phytoene, 0.2% to 2% by weight of phytofluene, trace amounts of β-carotene, γ-carotene, δ-carotene, vitamin E, phytosterols and phospholipids, and (b) 29% weight of a suitable encapsulating matrix exemplified by soya oil or pumpkin seed oil. One exemplary multi-carotenoids composition is a soft gel capsule weighing about 350 mg and comprising firstly, about 250 mg of a tomato oleoresin containing: (a) about 15 mg of lycopene, (b) about 1.5 mg of phytoene, (c) about 1.25 mg of phytofluene, (d) about 0.5 mg of vitamin E, (e) about 5 mg of β-carotene, (f) about 1.5 mg of a phytosterol, and (g) about 25 mg of a phospholipid, and secondly, about 100 mg of soya oil or alternatively, about 100 mg of pumpkin seed oil and the like. The soft gel capsule may be a nutritional supplement and/or a botanical drug.

Figure 2:
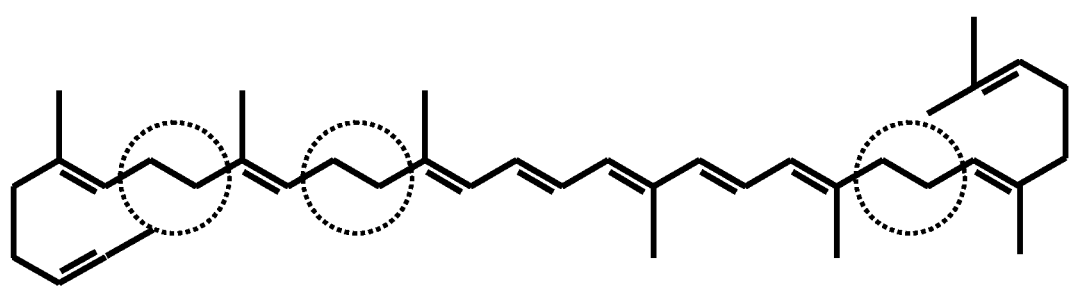
FIG. 2 is a phytoene isomer.
Figure 3:
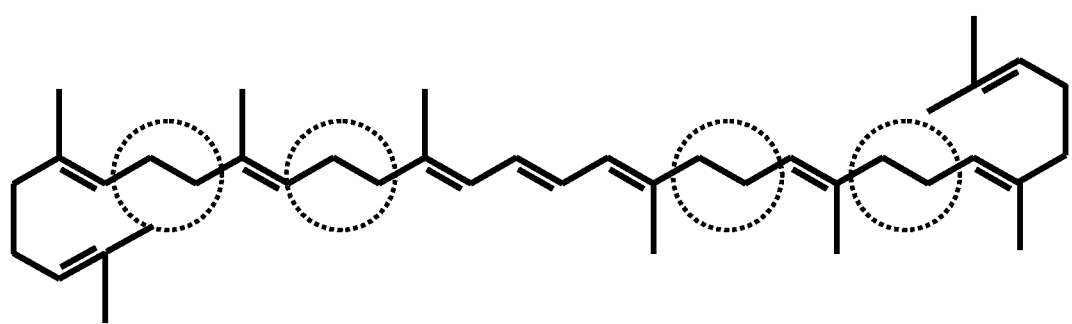
FIG. 3 is a phytofluene isomer.

In one embodiment, the multi-carotenoids composition of the present invention comprises at least one of an isomer of lycopene as exemplified in FIG. 1, an isomer of phytoene as exemplified in FIG. 2, and an isomer of phytofluene as exemplified in FIG. 3. Lycopene is an acyclic isomer of β-carotene. It is a 40 carbon atom, open chain polyisoprenoid with 11 conjugated double bonds and has the molecular formula $C_{40}H_{56}$. All-(E)-lycopene is the predominant geometric isomer found in plants. (Z)-isomers of lycopene are also found in nature, including (5Z)-, (9Z)-, (13Z)- and (15Z)-isomers. The structural formula of a preferred lycopene isomer is represented in FIG. 1. Phytoene is an intermediate in the biosynthesis of carotenoids and has the molecular formula $C_{40}H_{64}$. All-trans-phytoene is the predominant geometric isomer found in plants. The structural formula of a preferred phytoene isomer is represented in FIG. 2. Phytofluene is a product of carotenoid biosynthesis and has the molecular $C_{40}H^{62}$. All-trans-phytofluene is the predominant geometric isomer found in plants. The structural formula of a preferred phytofluene isomer is represented in FIG. 3.

In one embodiment, the multi-carotenoids composition may be administered for the treatment of aging-related urinary impairments and malfunctions in men. These aging-related urinary impairments and malfunctions in men are exemplified by benign prostatic hyperplasia, prostate cancer, lower urinary tract symptoms such as obstructive symptoms and irritative symptoms, and the like.

EXAMPLE 1

Effects of a Multi-Carotenoids Composition on Patients Exhibiting Urinary Impairments A 12-week phase II clinical study was initiated with a group of 74 males divided into two sub-groups of 37 individuals each, to assess the effects of an exemplary capsule formulation of the multi-carotenoids composition of the present invention. More specifically, the clinical study evaluated the potential effects of administration of a multi-carotenoids composition on serum PSA levels and LUTS. In particular, the study evaluated the effects of a multi-carotenoids composition administration on benign prostate hypertrophy (BPH). Twelve individuals were subsequently withdrawn from the study due to a screening failure. The remaining 63 subjects were divided into: (a) a first study group of 29 subjects who received a daily oral dose of one 350-mg capsule of the exemplary capsule of the present invention thereby providing a daily nutritional supplement of 15 mg of lycopene, and (b) a second study group of 32 subjects who received a daily oral dose of two 350-mg capsules of the present invention thereby providing a daily nutritional supplement of 30 mg of lycopene, on selected clinical parameters associated with prostate and urinary system health. The inclusion criteria for the trial were male subjects over 40 years of age with no prior history or indicators of prostate and/or other cancers, the subjects' prostate specific antigen (PSA) levels were between 2.5 and 20.0 ng/ml, and their renal and liver functions were within normal ranges. The exclusion criteria were individuals with fluctuating PSA levels, recent medical histories of urinary tract infection, prostatitis, acute urinary retention, individuals with known allergic reactions to carotenoids, individuals taking medications that may alter serum PSA levels as exemplified by 5-α reductase inhibitors, steroids or hormonal agents, and medications for lower urinary tract infections.

The trial followed a general protocol of, first, screening, evaluation and selection of the individuals for participating in the trial. Second, a 2-week washout period was undertaken during which the individuals maintained their normal lifestyle and eating habits while avoiding all lycopene foods such as tomato products, guava, pink grapefruits and the like. Third, at the end of the 2-week washout period, each individual's serum was sampled (i.e., the first sample) after which, they were assigned to one of the two study groups. Fourth, the individuals in each group received their daily dosage for 12 consecutive weeks. Each individual was sampled after one week (i.e., the second sample), after four weeks (i.e., the third sample) and after twelve weeks (i.e., the fourth sample). Each serum sample was assayed to quantitatively determine therein the PSA, lycopene, creatine, bilirubin, alanine amino transferase, hemoglobin, cholesterol, low-density lipoprotein, high-density lipoprotein, and testosterone levels. At each sampling time, the test individuals were also responded to questions regarding their urinary functions taken from the International Prostate Symptom Score (IPSS) index developed and validated by a multidisciplinary measurement committee of the American Urological Association (Fowler et al., 1992, Journal of Urology 148:1549-57). The 7 questions comprising the IPSS questionnaire may be classified into 2 categories: questions related to voiding or obstructive symptoms and questions related to storage or irritative symptoms questions. Subject's IPSS scores were used to evaluate the lower urinary tract symptoms (LUTS). Higher IPSS scores were indicative of individuals exhibiting a greater number of symptoms of LUTS.

The time "0" data (i.e., the first sample) are shown in Table 1. Individuals receiving a daily lycopene dose of 15 mg via one capsule of a multi-carotenoids composition of the exemplary composition of the present invention showed a 2.6 times increase in their serum lycopene levels, while individuals receiving a daily lycopene dose of 30 mg via two capsules of a multi-carotenoids composition daily showed a 3-fold increase in their serum lycopene levels (Table 2).

TABLE 1

Summary of test individual baseline data at the first sample time (0 time)*

| Parameter | Multi-carotenoids compositions - Lycopene dosage | | |
|---|---|---|---|
| | 15 mg/day | 30 mg/day | |
| Age (years) | 63.4 ± 8.1 | 63.9 ± 9.7 | P = 0.9 |
| Median PSA (ng/mL) | 8.8 ± 4.2 | 7.8 ± 3.8 | P = 0.3 |
| Median PSA range (ng/mL) | 3.5-18.4 | 2.7-17.5 | |
| IPSS | 11.3 ± 5.8 | 12.3 ± 6.5 | P = 0.5 |
| Body mass index | 24.6 ± 2.0 | 24.2 ± 2.9 | P = 0.9 |
| Serum total lycopene (ng/mL) | 297.9 ± 127.3 | 303.0 ± 162.3 | P = 0.9 |
| Serum creatine (mg/dL) | 1.07 ± 0.15 | 1.14 ± 0.15 | P = 0.06 |
| Serum bilirubin (mg/dL) | 0.9 ± 0.3 | 0.9 ± 0.3 | P = 0.4 |
| Alanine amino transferase (U/L) | 21.6 ± 7.9 | 18.5 ± 6.3 | P = 0.08 |
| Serum hemoglobin (mg/dL) | 14.4 ± 1.0 | 14.6 ± 1.2 | P = 0.5 |
| Serum cholesterol (mg/dL) | 198.4 ± 33.7 | 205.9 ± 32.5 | P = 0.4 |
| Low-density lipoprotein (mg/dL) | 122.5 ± 28.2 | 132.1 ± 54.9 | P = 0.4 |
| High-density lipoprotein (mg/dL) | 41.5 ± 9.2 | 44.2 ± 10.3 | P = 0.3 |
| Serum triglycerides (mg/dL) | 122.6 ± 53.1 | 115.6 ± 68.4 | P = 0.7 |
| Serum testosterone (mg/dL) | 4.5 ± 1.7 | 4.8 ± 1.9 | P = 0.5 |

*Data are means ± standard deviations

TABLE 2

Changes in serum lycopene levels after 12 weeks of supplementation with the exemplary composition of the present invention*.

| Sample time | Multi-carotenoids compositions - Lycopene dosage | | |
|---|---|---|---|
| | 15 mg/day | 30 mg/day | |
| Time "0" (baseline) | 279.9 ± 127.3 | 303.0 ± 162.3 | P = 0.9 |
| After 12 weeks | 780.0 ± 224.1 | 947.5 ± 290.4 | P = 0.01 |

*Serum lycopene levels are reported as ng./mL means ± standard deviations.

The median results indicated that the test individuals from both daily dosage groups showed marginal declines in their PSA levels over the 12-week study (Table 3). However, a sub-group of 23 test individuals with baseline PSA levels greater than 8.0 at the first sampling time (i.e., time "0"), from both treatment groups, showed significant decreases in their PSA levels over the 12-week study (Table 4).

TABLE 3

Changes in PSA levels during 12 weeks of supplementation with the exemplary composition of the present invention*.

| Sample time | Multi-carotenoids compositions - Lycopene dosage | |
|---|---|---|
| | 15 mg/day | 30 mg/day |
| Time "0" (baseline) | 8.8 ± 4.2 | 7.8 ± 3.7 |
| After 4 weeks | 8.3 ± 3.9 | 7.0 ± 3.8 |
| % change from baseline | −4% | −9% |
| | P = 0.08 | P = 0.01 |
| After 12 weeks | 8.0 ± 3.8 | 7.5 ± 4.0 |
| % change from baseline | −5.2% | −3.1% |
| | P = 0.17 | P = 0.22 |

*PSA data are reported as ng/mL means ± standard deviations.

TABLE 4

Changes in PSA levels in test individuals with elevated
baseline PSAs, during 12 weeks of supplementation with
the exemplary composition of the present invention.

| Sample time | PSA level (ng/mL) |
|---|---|
| Time "0" (baseline) | 12.4 ± 3.2 |
| After 4 weeks | 11.2 ± 4.1 |
| % change from baseline | −11% |
|  | P = 0.01 |
| After 12 weeks | 10.9 ± 4.0 |
| % change from baseline | −12% |
|  | P = 0.04 |

The test individuals from both daily dosage groups showed a progressive decline in their IPSS indices over the 12-week study (Table 5).

TABLE 5

Changes in test individuals' IPSS indices
during 12 weeks of supplementation with the exemplary
composition of the present invention*.

| | Multi-carotenoids compositions - Lycopene dosage | |
|---|---|---|
| Sample time | 15 mg/day | 30 mg/day |
| Time "0" (baseline) | 11.3 ± 5.8 | 12.3 ± 6.5 |
| After 4 weeks | 9.5 ± 5.0 | 9.0 ± 5.0 |
| % change from baseline | −14% | −24% |
|  | P = 0.002 | P < 0.001 |
| After 12 weeks | 9.1 ± 5.9 | 7.5 ± 4.0 |
| % change from baseline | −17% | −32% |
|  | P = 0.012 | P < 0.001 |

*IPSS data are reported as points means ± standard deviations.

Furthermore, the test individuals from both daily dosage groups showed progressive declines in their obstructive IPSS scores and their irritative IPSS scores over the 12-week study (Table 6).

TABLE 6

Changes in obstructive and irritative IPSS scores
during 12 weeks of supplementation with the exemplary
composition of the present invention*.

| | Multi-carotenoids compositions - Lycopene dosage | |
|---|---|---|
| Sample time | 15 mg/day | 30 mg/day |
| | Obstructive IPSS Scores* | |
| Time "0" (baseline) | 5.6 ± 3.7 | 6.9 ± 4.8 |
| After 4 weeks | 4.7 ± 2.9 | 4.9 ± 3.5 |
| % change from baseline | −0.4% | −22% |
|  | P = 0.04 | P < 0.001 |
| After 12 weeks | 4.7 ± 3.7 | 4.0 ± 3.7 |
| % change from baseline | −3.4% | −27% |
|  | P = 0.18 | P < 0.001 |
| | Irritative IPSS Scores* | |
| Time "0" (baseline) | 5.7 ± 3.0 | 5.4 ± 2.9 |
| After 4 weeks | 4.9 ± 2.7 | 4.1 ± 2.2 |
| % change from baseline | −11% | −16% |
|  | P = 0.009 | P < 0.001 |
| After 12 weeks | 4.4 ± 2.5 | 3.6 ± 2.0 |
| % change from baseline | −16% | −27% |
|  | P = 0.001 | P < 0.001 |

*Obstructive and irritative IPSS data are reported as score means ± standard deviations.

Data from this clinical study indicated that administration of a multi-carotenoids composition demonstrated positive effects on patients exhibiting urinary impairments. More specifically, the data suggested that the administration of a multi-carotenoids composition was associated with a significant decrease in IPSS and may improve LUTS, particularly LUTS that is suggestive of BPH in men.

EXAMPLE 2

Effects of a Multi-Carotenoids Composition on Patients Exhibiting Urinary Impairments A 12-week phase III double-blind, randomized, placebo-controlled, parallel study was initiated with a group of eligible male subjects to assess the effects of a multi-carotenoids composition. More specifically, the clinical study evaluated the potential effects of administration of a multi-carotenoids composition on serum PSA levels and LUTS. In particular, the study evaluated the potential effects of administration of a multi-carotenoids composition on benign prostate hypertrophy (BPH).

Individual subjects were divided into: (a) a first group of subjects who received a daily oral dose of a multi-carotenoids composition thereby providing a daily nutritional supplement of 30 mg of lycopene, and (b) a second group of subjects who received a daily oral dose of a placebo, based on selected clinical parameters associated with prostate and urinary system health.

The inclusion and exclusion criteria for the trial were similar to those outlined in Example 1 above.

The trial followed a general protocol of screening, evaluation and selection of the individuals for participating in the trial; administration of the daily supplements to the selected trial subjects over the course of the trial; and collection data samples from each of the selected trial subjects.

The effects of administration of a multi-carotenoids composition on each of the subjects were evaluated based on the data gathered and results were reviewed for the existence of a placebo effect. A placebo effect is the measurable, observable, or felt improvement in health or behaviour that is not attributable to a medication or invasive treatment that has been administered.

The embodiments of the present invention comprising multi-carotenoids compositions as disclosed herein for provision of a daily nutritional supplement and/or botanical drug of about 5 mg, at least about 10 mg, at least about 15, and at least 30 mg of lycopene, are useful for ameliorating the effects of aging-related impaired urinary functions in men, for example BPH, LUTS, prostate cancer and the like.

While particular exemplary embodiments of the present invention have been described in the foregoing, it is to be understood that other embodiments are possible within the scope of the present invention and are intended to be included herein. In view of numerous changes and variations that will be apparent to persons skilled in the art, the scope of the present invention is to be considered limited solely by the appended claims.

What is claimed is:

1. A method for treating benign prostate hyperplasia comprising administrating to a subject in need of such treatment an effective amount of a composition comprising
  (a) a tomato extract, comprising
    about 2% to 10% by weight of lycopene;
    about 0.25% to 2% by weight of phytoene; and
    about 0.2% to 2% by weight of phytofluene; and
  (b) a suitable carrier.

2. The method according to claim 1, wherein the composition further comprises at least one carotene selected from the group consisting of β-carotene, γ-carotene, and δ-carotene, a phytosterol, a tocopherol and a phospholipid.

3. The method according to claim 2, wherein said composition comprises about 1% to 3% by weight of a tocopherol; about 1% to 2% by weight of a β-carotene; about 0.3% to 0.6% by weight of a phytosterol; and about 5% to 10% by weight of a phospholipid.

4. The method according to claim 1, wherein the composition further comprises: an edible oil.

5. The method according to claim 4, wherein said edible oil is selected from the group consisting of soya oil, pumpkin seed oil, grape-seed oil and combinations thereof.

6. The method according to claim 1, wherein said composition comprises about 4% to 7% by weight of lycopene, about 0.4% to 0.7% by weight of phytoene, and about 0.3% to 0.6% by weight of phytofluene.

7. The method according to claim 1, wherein said composition comprises at least 5 mg to at least 30 mg of lycopene.

8. The method according to claim 4, wherein the composition comprises about 29% by weight of edible oil.

9. The method according to claim 1, wherein the composition is in the form of a nutritional supplement.

10. The method according to claim 1, wherein the composition is in the form of a botanical drug.

11. The method according to claim 1, wherein the subject's serum lycopene level increases, by 12 weeks post-administration, to at least 2.6 fold of the serum lycopene level before administration of the composition.

12. A method for reducing International Prostate Symptom Score (IPSS), comprising administrating to a subject in need of such reduction an effective amount of a composition comprising (a) a tomato extract, comprising
about 2% to 10% by weight of lycopene;
about 0.25% to 2% by weight of phytoene; and
about 0.2% to 2% by weight of phytofluene; and
(b) a suitable carrier.

13. The method according to claim 12, wherein the composition further comprises at least one carotene selected from the group consisting of 62 -carotene, γ-carotene, and δ-carotene, a phytosterol, a tocopheral and a phospholipid.

14. The method according to claim 13, wherein said composition comprises about 1% to 3% by weight of a tocopherol; about 1% to 2% by weight of a β-carotene; about 0.3% to 0.6% by weight of a phytosterol; and about 5% to 10% by weight of a phospholipid.

15. The method according to claim 12, wherein the composition further comprises: an edible oil.

16. The method according to claim 15, wherein said edible oil is selected from the group consisting of soya oil, pumpkin seed oil, grape-seed oil and combinations thereof.

17. The method according to claim 12, wherein said composition comprises about 4% to 7% by weight of lycopene, about 0.4% to 0.7% by weight of phytoene, and about 0.3% to 0.6% by weight of phytofluene.

18. The method according to claim 12, wherein said composition comprises at least 5 mg to 30 mg of lycopene.

19. The method according to claim 15, wherein the composition comprises about 29% by weight of edible oil.

20. The method according to claim 12, wherein the subject's serum lycopene level increases, by 12weeks post-administration, to at least 2.6 fold of the serum lycopene level before administration of the composition.

* * * * *